United States Patent
Sha

(10) Patent No.: US 12,419,239 B2
(45) Date of Patent: Sep. 23, 2025

(54) RICE CULTIVAR 'OZARK'

(71) Applicant: The Board of Trustees of the University of Arkansas, Little Rock, AR (US)

(72) Inventor: Xueyan Sha, Stuttgart, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 345 days.

(21) Appl. No.: 18/073,277

(22) Filed: Dec. 1, 2022

(65) Prior Publication Data

US 2024/0180098 A1    Jun. 6, 2024

(51) Int. Cl.
*A01H 6/46* (2018.01)
*A01H 5/10* (2018.01)

(52) U.S. Cl.
CPC ............ *A01H 6/4636* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 6,281,416 B1 | 8/2001 | Moldenhauer | |
| 7,141,725 B2 * | 11/2006 | Linscombe | A01H 5/10 800/320.2 |
| 7,429,697 B2 | 9/2008 | Moldenhauer | |
| 8,134,058 B2 | 3/2012 | Moldenhauer | |
| 9,398,750 B2 | 7/2016 | Moldenhauer et al. | |
| 9,877,452 B1 | 1/2018 | Moldenhauer et al. | |
| 10,791,697 B2 | 10/2020 | Wisdom et al. | |
| 2022/0095561 A1 | 3/2022 | Moldenhauer | |
| 2022/0104447 A1 | 4/2022 | Moldenhauer | |
| 2022/0125000 A1 | 4/2022 | Sha | |
| 2022/0132766 A1 | 5/2022 | Moldenhauer | |

OTHER PUBLICATIONS

Moldenhauer, K.A.K., et al. 2014. LaKast, A High Yielding, Very Short Season, Long-Grain Rice Variety. p. 74-80. in: Norman, R.J. and Moldenhauer, K.A.K. (eds.) B.R. Wells Rice Research Studies 2013. Arkansas Agricultural Experiment Station Research Series 617. Division of Agriculture, University of Arkansas.
Moldenhauer, K.A.K., et al. 2017. Diamond, a high yielding, very short season, long-grain rice variety. p. 68-74. in: Norman, R.J. and Moldenhauer, K.A.K. (eds.) B.R. Wells Rice Research Studies 2016. Arkansas Agricultural Experiment Station Research Series 643. Division of Agriculture, University of Arkansas.
U.S. Plant Variety Protection Application No. PV202300064 filed Nov. 22, 2022, Rice Cultivar Ozark, The Board of Trustees of the University of Arkansas.
U.S. Appl. No. 17/974,059, filed Oct. 26, 2022, Rice Cultivar Aroma 22, Debra Ahrent Wisdom, et al. inventor, The Board of Trustees of the University of Arkansas.

* cited by examiner

*Primary Examiner* — Vinod Kumar
(74) *Attorney, Agent, or Firm* — Quarles & Brady, LLP

(57) ABSTRACT

A rice cultivar designated 'Ozark' is disclosed herein. The present invention provides seeds, plants, and plant parts derived from rice cultivar Ozark. Further, it provides methods for producing a rice plant by crossing Ozark with itself or another rice variety. The invention also encompasses any rice seeds, plants, and plant parts produced by the methods disclosed herein, including those in which additional traits have been transferred into Ozark through the introduction of a transgene or by breeding Ozark with another rice cultivar.

19 Claims, No Drawings

RICE CULTIVAR 'OZARK'

BACKGROUND OF THE INVENTION

The present invention relates to a new and distinctive rice cultivar, designated Ozark.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valley of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season. In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in regions where rice is drill-seeded and a water-seeded nursery is used in regions where water-seeding is prominent.

Rice in the United States is classified into three primary market types by grain size, shape and chemical composition of the endosperm: long-grain, medium-grain, and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a rice cultivar designated Ozark. The invention encompasses the seeds, plants, and plant parts of rice cultivar Ozark, as well as plants with all the physiological and morphological characteristics of Ozark.

This invention also provides methods for producing a rice plant by planting a plurality of seeds or by crossing rice cultivar Ozark with itself or another rice line. Any plant breeding methods using rice cultivar Ozark are part of this invention, including selfing, backcrosses, hybrid production, and crosses to populations. All plants and seeds produced using rice cultivar Ozark as a parent are within the scope of this invention, including gene-converted plants of Ozark. Methods for introducing a gene into Ozark, either through traditional breeding or transformation, are also provided herein.

In still another aspect, the present invention provides regenerable cells for use in tissue culture of rice plant Ozark, as well as rice plants regenerated from these tissue cultures.

Definitions

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be backcrossed with one of the parental lines used to produce the $F_1$ hybrids.

Breeding. The genetic manipulation of living organisms.

Cell. A cell is the basic structural unit of all organisms. As used herein, this term includes isolated cells, cells grown in tissue culture, and cells that comprise a plant or plant part.

Cultivar. Used interchangeably with "variety". Refers to plants that have been cultivated by humans that have the characteristics of a particular genotype or combination of genotypes. Plants of a particular cultivar are distinguished from any other plants by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem, and leaves.

Essentially all the physiological and morphological characteristics. A plant having essentially all the physiological and morphological characteristics of the cultivar exhibits the characteristics of the cultivar with the exception of any characteristics derived from a converted gene.

$F_\#$. Denotes a filial generation, wherein the # is the generation number. For example, $F_1$ is the first filial generation.

Gene. Refers to a unit of inheritance corresponding to a distinct DNA sequence that forms part of a chromosome. A gene may encode a polypeptide or a functional nucleic acid molecule.

Gene-converted. Describes a plant wherein essentially all the desired physiological and morphological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernal length (L). Length of a rice grain measured in millimeters.

Kernal width (W). Width of a rice grain measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength."

Milling yield. A measure of the amount of rice kernels recovered after milling (i.e., the removal of hulls, bran, and germ). Milling yield is often expressed as a ratio of the amount of head rice (i.e., whole kernels) to the total amount of milled rice (i.e., whole and broken kernels). Both values are expressed as a weight percentage of the original paddy or rough rice sample that was milled. For example, for a sample of 100 grams of rough rice, a milling yield of 65:70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an $F_1$ rice plant produced from the cross of two rice plants, as well as plants produced from subsequent generational crosses (e.g., $F_2, F_3, F_4, F_5, F_6, F_7, F_8, F_9,$ and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like.

Trait. Refers to a measurable and/or observable characteristic of an organism.

Transgenic. Describes an organism or cell that contains genetic material that has been artificially introduced.

Wild-type. Used to refer to a gene that is common throughout a population and is, thus, arbitrarily designated the "normal" or "wild-type" form of the gene.

DETAILED DESCRIPTION OF THE INVENTION

The present invention provides a new and distinct rice cultivar designated Ozark. The invention encompasses both the seeds of this cultivar and plants grown from these seeds. The invention further encompasses any rice plant having all or essentially all the physiological and morphological characteristics of rice cultivar Ozark.

Development and characterization of rice cultivar Ozark: Ozark (Poaceae Oryzea *Oryza sativa* L.) is a high yielding, early maturing, conventional stature, long-grain rice cultivar developed in Stuttgart, Arkansas. It was selected from cross number 16CRS376 of 'Diamond' (U.S. Pat. No. 9,877,452)/ 'LaKast' (U.S. Pat. No. 9,398,750) made in summer 2016. Diamond and LaKast are typical US long-grain rice cultivars developed by Dr. Karen Moldenhauer (Moldenhauer et al., 2016; Moldenhauer et al., 2014).

Ozark was initiated as an $F_3$ bulk of single progeny row 18B2278 in a winter nursery near Lajas, Puerto Rico in spring 2019. It was evaluated in the preliminary Stuttgart Initial Trial (SIT) in summer 2019 as entry 19SIT1123 where it ranked second among 409 long-grain lines and commercial checks. Therefore, in 2020, this cultivar was advanced to the Arkansas Rice Performance Trials (ARPT), the Cooperative Uniform Regional Rice Nursery (URRN), and the Advanced/Elite Line Yield Trial (AYT) with the experimental designation RU2001185.

Ozark has demonstrated an outstanding grain yield, good milling yields, excellent grain quality, and improved lodging tolerance as compared with Diamond in 26 statewide and regional replicated trials during 2020-2021. At 120 g kg$^{-1}$ moisture, the average grain yield of Ozark is 219 bushels/ acre which compares favorably to Diamond's 211 bushels/ acre. The average milling yields (g kg$^{-1}$ whole milled kernels: g kg$^{-1}$ total milled rice) in those trials were 581:698 for Ozark and 564:690 for Diamond. Ozark has an average plant height of 43 inches when measured from soil surface to the tip of panicle of the main stem based on yield trials performed across the Mid-South, which is 2 inches taller than Diamond. Ozark appears to be moderately susceptible to lodging. Ozark matures slightly earlier than Diamond, averaging 88 days from emergence to 50% heading. It is adapted to the Southern US growing region.

Ozark has the typical U.S. long-grain rice cooking characteristics, similar to Diamond, and a slightly longer and plumper kernel than Diamond. Analyses conducted by Riceland Foods, Inc. (Stuttgart, AR) on 10 different sets of samples collected across Arkansas in 2020 showed that the average length (mm), width (mm), length/width ratio, and kernel weight (mg) of milled whole kernels of Ozark were 7.45, 2.14, 3.49, and 22.12, respectively, as compared to 7.23, 2.12, 3.41, and 21.58 for Diamond. Ozark had an average chalkiness value of 2.3%, which is similar to that of Diamond (2.25%). The average apparent amylose content of Ozark is 241 g kg$^{-1}$, which is slightly higher than that of Diamond (223 g kg$^{-1}$). Ozark has an intermediate gelatinization temperature of 69.3° C., which is similar to that of Diamond (69.6° C.).

Under both inoculated and natural infestation conditions, Ozark was rated susceptible to leaf blast (caused by *Pyricularia grisea* (Cooke) Sacc.) and neck blast that is caused by *Pyricularia grisea* (Cooke) Sacc. It was also rated susceptible to sheath blight (caused by *Rhizoctonia solani* Kuhn) and bacterial panicle blight (caused by *Burkholderia glumae*).

The leaves, lemma, and palea of Ozark are glabrous. The spikelet is straw colored. The apiculus is purple colored at heading but fades as the grains approach maturity. The grain is non-aromatic.

Variants observed and removed from fields of Ozark were primarily taller and earlier. Other variants included any combination of the following: pubescent, shorter, later, short-grain, medium-grain, intermediate-grain, gold and black hull, and sterile panicle. The total number of variants numbered less than 1 per 2000 plants.

The above-mentioned characteristics of rice cultivar Ozark are based primarily on data collected in Stuttgart, Arkansas and are summarized in Table 1. The developmental timeline for Ozark is shown in Table 2. The results of the rice performance trials (ARPT 2020-2021, URRN 2020-2021, and AYT 2020-2021) are detailed in Tables 3-15. Disease evaluation data is shown in Tables 16 and 17. The data were collected from the Advanced Elite Line Yield Trial (AYT) at RREC near Stuttgart, Pine Tree Experiment Station (PTST) near Colt, AR, and Northeast Research and Extension Center (NEREC) in Keiser; and URRN in Crowley, LA, Stuttgart, AR, Stoneville, MS, Malden, MO (2020 only), and Beaumont, TX; ARPT in Clay Co., Desha Co., RREC, Stuttgart, PTST, NEREC, Northeast Rice Research and Extension Center (NERREC, 2021 only), and Malden, MO (2020 only).

TABLE 1

| Cultivar description information |
|---|
| Plant: |
| Grain type: Long |
| Days to maturity (Seeding to 50% heading): 88 |

TABLE 1-continued

| Cultivar description information |
|---|
| Plant height: 110 cm |
| Plant color at booting: Green |
| Culm: |
| Angle (degrees from perpendicular after flowering): Erect (less than 30°) |
| Flag leaf (after heading): |
| Pubescence: Glabrous |
| Leaf angle: Erect |
| Blade color: Green |
| Panicle: |
| Length: 22.8 cm |
| Type: Compact |
| Exertion (near maturity): Moderately well |
| Axis: Droopy |
| Shattering (at maturity): Low (1-5%) |
| Grain (spikelet): |
| Awns (after full heading): Short and partly awned |
| Apiculus color: Purple |
| Stigma color: Light green |
| Lemma and palea color (at maturity): Straw |
| Lemma and palea pubescence: Glabrous |
| Grain (seed): |
| Seed coat color: Light brown |
| Scent: Nonscented |
| Size: 25.5 g/1000 seeds milled rice |
| Shape class (length/width ratio): |
| Paddy: Long (3.4:1 and more) |
| Brown: Long (3.1:1 and more) |
| Milled: Long (3.0:1 and more) |
| Disease resistance: |
| Rice blast (*Pyricularia grisea* (Cooke) Sacc.): Moderately susceptible |
| Sheath blight (*Rhizoctonia solani* Kuhn): Susceptible |
| False smut (*Ustilaginoidea virens* (Cooke) Takah.): Susceptible |
| Bacterial panicle blight (*Burkholderia glumae* and *B. gladioli*): Susceptible |

TABLE 2

Development timeline of Ozark

| Year | Generation | Designation | Trial | Comments |
|---|---|---|---|---|
| 2016 | Cross | 16CRS376 | | |
| 2017 | F1 | 17TP309 | Transplant | |
| 2018 | F2 | 18A3276-300 | Space-planted F2 Population | Puerto Rico |
| 2018-19 | F3 | 18B2278 | Progeny Row, Bulk | Puerto Rico |
| 2019 | F4 | 19SIT1123 | Stuttgart Initial Trials (SIT) | |
| 2020 | F5 | RU2001185 | Uniform Regional Rice Nursery (URRN) | |
| 2020 | F5 | 20AYT77 | Advanced/Elite Line Yield Trial (AYT) | |
| 2020 | F5 | 20ARPT E142 | Arkansas Rice Performance Trial (ARPT) | |
| 2021 | F6 | RU2001185 | Uniform Regional Rice Nursery (URRN) | |
| 2021 | F6 | 21AYT77 | Advanced/Elite Line Yield Trial (AYT) | |
| 2021 | F6 | 21ARPT E14 | Arkansas Rice Performance Trial (ARPT) | |
| 2021-22 | F7 | RU2001185 | Breeder Headrow Increase | Puerto Rico |
| 2021-22 | F7 | RU2001185 | Breeder Seed Production | Puerto Rico |
| 2022 | F8 | RU2001185 | Foundation Seed Production | |

TABLE 3

Overall average grain yield (at 12% H₂O) and milling yields (% head and total rice), 2020-2021

| Cultivar | Grain Yield (Bu/A) | Grain Yield (Lb/A) | Milling Yield (%) Head Rice | Milling Yield (%) Total Rice |
|---|---|---|---|---|
| Ozark | 219 | 9,836 | 58.1 | 69.8 |
| Diamond | 211 | 9,494 | 56.4 | 69.0 |
| No. trials | 26 | 26 | 23 | 23 |

TABLE 4

Overall average days to 50% heading, plant height, and lodging incidence, 2020-2021

| Cultivar | Seedling vigor† | Days to 50% heading | Plant height (inch) | Lodging incidence (%) |
|---|---|---|---|---|
| Ozark | 3.1 | 88 | 41 | 6.0 |
| Diamond | 3.1 | 88 | 40 | 1.3 |
| No. trials | 7 | 25 | 26 | 26 |

†Subjective rating on a scale of 1-7: 1 = perfect stand and 7 = no stand

TABLE 5

Kernel dimensions and weight of milled rice analyzed by Riceland Foods, Inc., Stuttgart, Arkansas using ARPT samples collected across the state, 2020-2021

| Cultivar | Length (L) mm | Width (W) mm | Thickness mm | L/W ratio | Kernel weight (mg) |
|---|---|---|---|---|---|
| Ozark | 7.45 | 2.14 | 1.71 | 3.49 | 22.12 |
| Diamond | 7.23 | 2.12 | 1.72 | 3.41 | 21.58 |
| No. trials | 10 | 10 | 10 | 10 | 10 |

TABLE 6

Rapid viscosity analysis (RVA) results measured in Rapid-Visco Analyser units (RVU) analyzed by Riceland Foods, Inc., Stuttgart, Arkansas using ARPT samples collected across the state, 2020

| Cultivar | Peak Viscosity | Trough | Breakdown | Final Viscosity | Setback |
|---|---|---|---|---|---|
| Ozark | 233 | 115 | 118 | 263 | 31 |
| Diamond | 236 | 114 | 122 | 254 | 18 |
| No. trials | 10 | 10 | 10 | 10 | 10 |

TABLE 7

Average grain yield in the ARPT at six Arkansas locations, 2020-2021

Grain yield (bushels/acre at 12% H₂O)

| Cultivar | Clay† | Desha | NEREC | NRREC | PTRS | RREC | Mean |
|---|---|---|---|---|---|---|---|
| Ozark | 253 | 189 | 215 | 215 | 208 | 256 | 219 |
| Diamond | 248 | 195 | 214 | 194 | 181 | 194 | 204 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR. Trials at NRREC were conducted in 2021 only

TABLE 8

Average milling yields in the ARPT at six Arkansas locations, 2020-2021

Milling yields (% head rice-% total rice)

| Cultivar | Clay† | Desha | NEREC | NRREC | PTRS | RREC | Mean |
|---|---|---|---|---|---|---|---|
| Ozark | 59-71 | 61-70 | 61-71 | 63-71 | 58-70 | 59-70 | 60-70 |
| Diamond | 54-70 | 61-70 | 62-71 | 63-71 | 59-69 | 59-69 | 59-70 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR. Trials at NRREC were conducted in 2021 only

TABLE 9

Overall agronomical characteristics in the ARPT at six Arkansas locations, 2020-2021

| Cultivar | Days to 50% heading | Canopy Height (inch) | Lodging (%) |
|---|---|---|---|
| Ozark | 86 | 38 | 1.9 |
| Diamond | 87 | 38 | 1.4 |

TABLE 10

Grain yield in the 2021 ARPT at six Arkansas locations

Grain yield (bushels/acre at 12% H₂O)

| Cultivar | Clay† | Desha | NEREC | NRREC | PTRS | RREC | Mean |
|---|---|---|---|---|---|---|---|
| Ozark | 236 | 171 | 241 | 215 | 210 | 233 | 218 |
| Diamond | 226 | 165 | 238 | 194 | 179 | 220 | 204 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR

TABLE 11

Milling yields in the 2021 ARPT at six Arkansas locations

Milling yield (% head rice-% total rice)

| Cultivar | Clay† | Desha | NEREC | NRREC | PTRS | RREC | Mean |
|---|---|---|---|---|---|---|---|
| Ozark | 54-69 | 64-71 | 61-71 | 63-71 | 55-69 | 55-68 | 59-70 |
| Diamond | 54-69 | 64-71 | 61-71 | 63-71 | 55-69 | 57-68 | 59-70 |

†Test location: Clay = Clay Co., AR., Desha = Desha Co., AR., NEREC = Northeast Research and Extension Center at Keiser, AR., NRREC = Northeast Rice Research and Extension Center at Harrisburg, AR., PTRS = Pine Tree Research Station near Colt, AR., and RREC = Rice Research and Extension Center near Stuttgart, AR

TABLE 12

Grain yield in the 2020 ARPT at five Arkansas locations

Grain yield (bushels/acre at 12% H₂O)

| Cultivar | Clay† | Desha | NEREC | PTRS | RREC | Mean |
|---|---|---|---|---|---|---|
| Ozark | 270 | 208 | 188 | 205 | 179 | 210 |
| Diamond | 270 | 226 | 190 | 183 | 169 | 208 |

†Test location: Clay = Clay Co., AR., Desha = Desha Co., AR., NEREC = Northeast Research and Extension Center at Keiser, AR., PTRS = Pine Tree Research Station near Colt, AR., and RREC = Rice Research and Extension Center near Stuttgart, AR

TABLE 13

Milling yields in the 2020 ARPT at five Arkansas locations Cultivar

| | Milling yields (% head rice-% total rice) | | | | |
|---|---|---|---|---|---|
| Cultivar | Clay† | Desha | NEREC | PTRS | RREC | Mean |
| Ozark | 63-72 | 58-70 | 61-70 | 61-71 | 63-71 | 61-71 |
| Diamond | 59-71 | 58-70 | 62-71 | 60-70 | 61-70 | 60-70 |

†Test location: Clay = Clay Co., AR., Desha = Desha Co., AR., NEREC = Northeast Research and Extension Center at Keiser, AR., PTRS = Pine Tree Research Station near Colt, AR., and RREC = Rice Research and Extension Center near Stuttgart, AR.

TABLE 14

Average yield, milling, and agronomical characteristics in URRN trials conducted in Stuttgart, AR, Crowley, LA, Stoneville, MS, and Beaumont, TX, 2020-2021

| Cultivar | Days to 50% heading | Height (cm) | Lodging (%) | Yield (bu/A) | Yield (lb/A) | Head rice (%) | Total rice (%) |
|---|---|---|---|---|---|---|---|
| | | | 2020-2021 Average | | | | |
| Ozark | 90 | 108 | 17 | 213 | 9,575 | 54.6 | 69.5 |
| Diamond | 90 | 104 | 3 | 210 | 9,452 | 52.1 | 68.5 |
| | | | 2020 | | | | |
| Ozark | 90 | 109 | 34 | 211 | 9,480 | 58.0 | 70.0 |
| Diamond | 91 | 105 | 5 | 211 | 9,478 | 55.9 | 68.1 |
| | | | 2021 | | | | |
| Ozark | 89 | 107 | 0 | 215 | 9,694 | 51.2 | 69.0 |
| Diamond | 89 | 103 | 0 | 209 | 9,420 | 48.3 | 68.8 |

TABLE 15

Performance in the AYT conducted at Northeast Research and Extension Center (NEREC), Pine Tree Research Station (PTRS), and Rice Research and Extension Center (RREC), 2020-2021

| Cultivar | Seedling vigor† | Days to 50% heading | Plant height (inch) | Lodging (%) | Yield (bu/A) | Head rice (%) | Total rice (%) |
|---|---|---|---|---|---|---|---|
| | | | 3-Location Average | | | | |
| Ozark | 3.1 | 88 | 43 | 0 | 244 | 60.2 | 69.0 |
| Diamond | 3.3 | 88 | 41 | 0 | 228 | 56.6 | 67.4 |
| | | | RREC | | | | |
| Ozark | 3.0 | 87 | 44 | 0 | 256 | 57.2 | 67.5 |
| Diamond | 3.0 | 88 | 44 | 0 | 244 | 54.7 | 66.3 |
| | | | PTRS | | | | |
| Ozark | 3.0 | 88 | 44 | 0 | 242 | 61.7 | 69.7 |
| Diamond | 3.7 | 90 | 42 | 0 | 223 | 59.1 | 68.1 |
| | | | NEREC | | | | |
| Ozark | 3.3 | 88 | 43 | 0 | 240 | 60.1 | 69.1 |
| Diamond | 3.3 | 85 | 39 | 0 | 226 | 53.2 | 67.0 |

†Subjective rating on a scale of 1-7: 1 = perfect stand and 7 = no stand

TABLE 16

Disease reactions of rice cultivars inoculated with different races of the blast pathogen (*Pyricularia oryzae*) in a greenhouse in Stuttgart, AR, 2020-2021

| Cultivar | IB-1 | IB-17 | IB-49 | IC-17 | IE1-K |
|---|---|---|---|---|---|
| Ozark | MS† | S | S | MS | MS |
| Diamond | S | S | MS | S | S |
| No. trials | 2 | 2 | 2 | 2 | 2 |

†Disease reaction, R = resistant, MR = moderately resistant, MS = moderately susceptible, and S = susceptible.

TABLE 17

Diseases reactions of rice cultivar Ozark under natural infestation in trials across Arkansas, 2020-2021

| Sheath Blight | Blast | Straight-head | Bacterial Panicle Blight | Narrow Brown Leaf Spot | Stem Rot | Kernel Smut | False Smut | Lodging | Black Sheath Rot | Sheath Spot |
|---|---|---|---|---|---|---|---|---|---|---|
| S | S | MR | — | MS | — | — | MS | — | — | — |

Reaction: R = Resistant; MR = Moderately Resistant; MS = Moderately Susceptible; S = Susceptible; VS = Very Susceptible Methods This present invention provides methods for producing rice plants. In some embodiments, these methods involve crossing a first parent rice plant with a second parent rice plant, wherein either the first or second parent rice plant is an Ozark rice plant. Further, both the first and second parent rice plants can come from rice cultivar Ozark. This invention is also directed to methods for producing an Ozark-derived rice plant by crossing rice cultivar Ozark with a second rice plant, growing the progeny seed, and repeating the crossing and growing steps with the Ozark-derived plant from 0 to 7 times. Any such methods using rice cultivar Ozark are part of this invention, including selfing, backcrosses, hybrid production, crosses to populations, and the like. All plants produced using rice cultivar Ozark as a parent are within the scope of this invention, including plants derived from rice cultivar Ozark. In some embodiments, rice cultivar Ozark is used in crosses with other, different, rice cultivars to produce first generation ($F_1$) rice seeds and plants with superior characteristics.

In some embodiments, an Ozark progeny plant is selected that has molecular markers, morphological characteristics, and/or physiological characteristics in common with Ozark (e.g., those listed in Table 1). Techniques such as RFLP-enhanced selection, genetic marker enhanced selection (e.g., SSR markers), and the making of double haploids may be utilized to identify progeny that share particular traits with Ozark.

Further, this invention provides methods for introducing a desired trait into rice cultivar Ozark. This may be accomplished using traditional breeding methods, such as backcrossing (see the section titled "Breeding Methods" below). Alternatively, the desired trait may be introduced by transforming the rice cultivar with a transgene (see the section title "Transformation Methods" below). The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps that involve producing rice seed from the resulting rice plants and/or planting the rice seed.

The present invention encompasses all plants and parts thereof produced by the methods described herein, as well as the seeds produced by these plants. Further, any plants derived from rice cultivar Ozark or produced from a cross using cultivar Ozark are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar Ozark comprising a combination of at least two traits of Ozark selected from those described in the Tables and Detailed Description of the Invention. The progeny rice plant should not be significantly different from Ozark for said traits, as determined at the 5% significance level when grown in the same environment. Those of skill in the art know how to compare a trait between two plant varieties to determine if there is a significant difference between them (Fehr and Walt, Principles of Cultivar Development, pp. 261-286 (1987)). Molecular markers or mean trait values may be used to identify a plant as progeny of Ozark. Alternatively, progeny may be identified through their filial relationship with rice cultivar Ozark (e.g., as being within a certain number of breeding crosses of rice cultivar Ozark). For example, progeny produced by the methods described herein may be within 1, 2, 3, 4, or 5 breeding crosses of rice cultivar Ozark.

Tissue Culture:

The present invention provides tissue cultures of regenerable cells or protoplasts produced from rice cultivar Ozark. As is well known in the art, tissue culture of rice can be used for the in vitro regeneration of a rice plant. Thus, such cells and protoplasts may be used to produce plants having all the physiological and morphological characteristics of rice variety Ozark. The rice plants regenerated by these methods are also encompassed by the present invention.

As used herein, the term "tissue culture" describes a composition comprising isolated plant cells or a collection of such cells organized into parts of a plant. Exemplary tissues for culture include protoplasts, calli, plant clumps, embryos, pollen, flowers, seeds, pods, leaves, stems, roots, root tips, and anthers. Culture of various rice tissues and regeneration of plants therefrom is well known in the art.

Breeding Methods:

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar Ozark in any plant breeding method is encompassed by the present invention. The choice of a breeding or selection method will depend on several factors, including the mode of plant reproduction, the heritability of the trait(s) being improved, and the type of cultivar used commercially (e.g., $F_1$ hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the $F_4$ generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods:

As is noted above, the present invention provides plants and seeds of rice cultivar Ozark in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is a DNA molecule comprising a gene operatively linked to a regulatory element (e.g., a promoter) that drives its expression in a cell. The expression vector may contain one or more such gene/regulatory element combinations. The expression vector may also include additional sequences, such as a signal sequence or a tag, that modify the protein produced by the transgene.

Expression vectors typically include at least one genetic marker that allows transformed cells containing the vector to be recovered by selection. In some embodiments, negative selection (i.e., inhibiting the growth of cells that do not contain the selectable marker gene) is utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and green fluorescent protein (GFP).

Transgene expression is typically driven by operably linking the transgene to a promoter within the expression vector. However, other regulatory elements may also be used to drive transgene expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be tissue-specific, cell type-specific, inducible, or constitutive. Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement,* 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch, et al., *Science,* 227:1229 (1985). Descriptions of *Agrobacterium* vector systems and methods for *Agrobacterium*-mediated gene transfer are provided by Gruber, et al., supra.

REFERENCES

Moldenhauer, K. A. K., Sha, X., Berger, G. L., Hardke, J. T., Norman, R. J., Wilson Jr., C. E., Wamishe, Y., Cartwright, R. D., Blocker, M. M., McCarty, D., Ahrent, D. K., Boyett, V. A., Frizzell, D. L., Bulloch, J. M., Castaneda-Gonzalez, E., Kelsey, C. D., and Belmar, S. 2014. LaKast, A High Yielding, Very Short Season, Long-Grain Rice Variety. p. 74-80. In Norman, R. J. and Moldenhauer, K. A. K. (eds.) B. R. Wells Rice Research Studies 2013. Arkansas Agricultural Experiment Station Research Series 617. Division of Agriculture, University of Arkansas.

Moldenhauer, K. A. K., Sha, X., Shakiba, E., Wisdom, D. K. A., Blocker, M. M., Hardke, J., Wamishe, Y., Norman, R. J., McCarty, D. L., Northcutt, C. H., Boyett, V. A., Frizzell, D. L., Belmar, S. B., Thompson, V. I., Bulloch, J. M., Castaneda-Gonzalez, E., and Kelsey, C. 2017. Diamond, a high yielding, very short season, long-grain rice variety. p. 68-74. In Norman, R. J. and Moldenhauer, K. A. K. (eds.) B. R. Wells Rice Research Studies 2016. Arkansas Agricultural Experiment Station Research Series 643. Division of Agriculture, University of Arkansas.

DEPOSIT INFORMATION

A deposit of the University of Arkansas Division of Agriculture Rice Research and Extension Center proprietary rice cultivar Ozark disclosed above and recited in the appended claims has been made with the Provasoli-Guillard National Center for Marine Algae and Microbiota (NCMA) (60 Bigelow Drive, East Boothbay, ME 04544). The date of deposit was May 1, 2023. The deposit of 625 seeds was taken from the same deposit maintained by the University of Arkansas Division of Agriculture Rice Research and Extension Center (2900 Hwy 130 E., Stuttgart, AR 72160) since prior to the filing date of this application. All restrictions will be irrevocably removed upon granting of a patent, and the deposit is intended to meet all of the requirements of 37 C.F.R. §§ 1.801-1.809. The Accession Number provided by the International Depositary Authority is 202305004. The deposit will be maintained in the depository for a period of thirty years, or five years after the last request, or for the enforceable life of the patent, whichever is longer, and will be replaced as necessary during that period.

What is claimed is:

1. A rice seed of the cultivar 'Ozark,' a representative sample of seed of said cultivar having been deposited under National Center for Marine Algae and Microbiota International Depositary Authority Accession No. 202305004.

2. A rice plant, or a part thereof, produced by growing the seed of claim 1.

3. A rice plant, or a part thereof, having all of the physiological and morphological characteristics of the rice plant of claim 2.

4. Pollen or an ovule of the plant of claim 2.

5. A method for producing rice plants, said method comprising planting a plurality of rice seeds as recited in claim 1 under conditions favorable for the growth of rice plants.

6. The method of claim 5, further comprising the step of producing rice seed from the resulting rice plants.

7. A rice seed produced by the method of claim 6, wherein the rice seed is capable of growing into a plant having all of the physiological and morphological characteristics of the rice plant.

8. A tissue culture of regenerable cells or protoplasts produced from the rice plant of claim 2.

9. The tissue culture of claim 8, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

10. A rice plant regenerated from the tissue culture of claim 8, said rice plant having all of the physiological and morphological characteristics of 'Ozark'.

11. A method for producing an F hybrid rice plant, said method comprising crossing a first parent rice plant with a second parent rice plant, wherein the first parent rice plant or the second patent rice plant is the rice plant of claim 2.

12. The method of claim 11, further comprising the step of producing rice seed from the resulting rice plant.

13. An $F_1$ rice seed produced by the method of claim 12.

14. The method of claim 11, wherein the second parent rice plant is transgenic.

15. A method comprising transforming the rice plant of claim 2 or cell thereof with a transgene, wherein the transgene confers at least one trait selected from the group consisting of: herbicide resistance, insect resistance, bacterial resistance, fungal resistance, viral resistance, modified fatty acid metabolism, modified carbohydrate metabolism, and male sterility.

16. A rice plant or part thereof, or rice seed, produced by the method of claim 15.

17. An herbicide resistant rice plant produced by the method of claim 15, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

18. A method of introducing a desired trait into rice cultivar 'Ozark,' said method comprising the steps of:
   (a) crossing plants as recited in claim 2 with plants of another rice line expressing the desired trait, to produce progeny seeds;
   (b) growing the progeny seeds to produce progeny plants and selecting the progeny plants that express the desired trait, to produce selected progeny plants;
   (c) crossing the selected progeny plants with plants as recited in claim 2 to produce new progeny plants;
   (d) selecting the new progeny plants that express the desired trait; and
   (e) repeating steps (c) and (d) three or more times in succession, to produce selected higher generation backcross progeny plants that express both the desired trait and essentially all of the physiological and morphological characteristics of rice cultivar 'Ozark', as described in the specification, determined at a 5% significance level, when grown in the same environmental conditions.

19. The method of claim 18, additionally comprising the step of planting a plurality of rice seed produced by selecting higher generation backcross progeny plants under conditions favorable for the growth of rice plants and optionally comprising the step of producing rice seed from the resulting rice plants.

* * * * *